United States Patent
Burkhart

(10) Patent No.: US 8,202,296 B2
(45) Date of Patent: *Jun. 19, 2012

(54) TECHNIQUE FOR TISSUE FIXATION BY CAPTURING AND ANCHORING A LINK OF SUTURE CHAIN ATTACHED TO TISSUE

(75) Inventor: Stephen S. Burkhart, San Antonio, TX (US)

(73) Assignee: Arthrex, Inc., Naples, FL (US)

( * ) Notice: Subject to any disclaimer, the term of this patent is extended or adjusted under 35 U.S.C. 154(b) by 263 days.

This patent is subject to a terminal disclaimer.

(21) Appl. No.: 12/488,325

(22) Filed: Jun. 19, 2009

(65) Prior Publication Data

US 2009/0318959 A1    Dec. 24, 2009

Related U.S. Application Data

(60) Provisional application No. 61/074,104, filed on Jun. 19, 2008.

(51) Int. Cl.
    *A61B 17/04*    (2006.01)
(52) U.S. Cl. ....................................................... 606/232
(58) Field of Classification Search .................. 606/139, 606/144, 228, 232, 300, 301, 224
    See application file for complete search history.

(56) References Cited

U.S. PATENT DOCUMENTS

| | | | |
|---|---|---|---|
| 5,891,168 A * | 4/1999 | Thal | 606/232 |
| 6,527,795 B1 * | 3/2003 | Lizardi | 606/232 |
| 2007/0135843 A1 * | 6/2007 | Burkhart | 606/232 |
| 2007/0191849 A1 | 8/2007 | ElAttrache et al. | |
| 2008/0004659 A1 | 1/2008 | Burkhart et al. | |
| 2008/0009904 A1 * | 1/2008 | Bourque et al. | 606/232 |
| 2008/0208253 A1 | 8/2008 | Dreyfuss et al. | |
| 2009/0287246 A1 * | 11/2009 | Cauldwell et al. | 606/232 |

OTHER PUBLICATIONS

"Athrex is Reaching New Heights in Rotator Cuff Repair." Athrex, Inc. 2007.*

* cited by examiner

*Primary Examiner* — Ryan Severson
*Assistant Examiner* — Katherine M Shi
(74) *Attorney, Agent, or Firm* — Dickstein Shapiro LLP

(57) ABSTRACT

A method and device for knotless fixation of tissue. The method utilizes a push-in type anchor (for example, a self-punching anchor) and a suture chain that includes a plurality of loops. A first portion of the suture chain is secured to the tissue to be fixated. The suture chain is next secured to the push-in type anchor (for example, by passing the suture chain through an eyelet of the anchor). The anchor is then advanced along the suture chain to bring a tip of the anchor above a chosen loop or link of the suture chain. The tip of the anchor is pushed through the chosen loop so that the tip locks the chosen loop in place (for example, by capturing both sides of the link above a shoulder of the anchor). With the captured link, the anchor is advanced into a pilot hole or socket formed in the bone to fixate the tissue. The captured link provides a hard stop that does not slip, in addition to frictional interference between the anchor and the bone socket.

12 Claims, 5 Drawing Sheets

TECHNIQUE FOR TISSUE FIXATION BY CAPTURING AND ANCHORING A LINK OF SUTURE CHAIN ATTACHED TO TISSUE

CROSS-REFERENCE TO RELATED APPLICATIONS

This application claims the benefit of U.S. Provisional Application No. 61/074,104, filed Jun. 19, 2008, the entire disclosure of which is incorporated by reference herein.

FIELD OF THE INVENTION

The present invention relates to surgical fixation and, more particularly, to methods of conducting anatomical tissue repair, such as ligament repair and reconstruction, using a technique for tissue fixation by capturing and anchoring a link of suture chain attached to tissue.

BACKGROUND OF THE INVENTION

When soft tissue such as a ligament or a tendon becomes detached from a bone, surgery is usually required to reattach or reconstruct the tissue. Often, a tissue graft is attached to the bone to facilitate re-growth and permanent attachment. Various fixation devices, including sutures, screws, staples, wedges, and plugs have been used in the past to secure soft tissue to bone. For example, in typical interference screw fixation, the graft is fixed to the bone by driving the screw into a blind hole or a tunnel in the bone while trapping the end of the graft between the screw and the bone tunnel. In other methods, the graft is simply pinned against the bone using staples or sutures tied around the end of the graft to the bone.

U.S. Application Publ. No. 2008/0208253, the disclosure of which is incorporated by reference herein, discloses a surgical technique and associated instruments for securing soft tissue to bone which does not require the surgeon to tie suture knots to secure the tissue to the bone. According to this technique, a cannulated plug or screw is pre-loaded onto a distal end of a cannulated driver provided with an eyelet implant at its distal end. A suture attached to the graft is passed through the eyelet of the implant located at the distal end of the driver. The distal end of the driver together with the eyelet implant is inserted into bone (if the implant is self-punching) or is inserted into the bottom of a pre-formed hole, with the screw or plug disposed just outside the hole. Tension is applied to the suture to position the graft at the desired location relative to the bone hole. The screw or plug is then fully advanced into the pilot hole by turning the interference screw or tapping the plug until the cannulated screw or plug securely engages and locks in the eyelet implant, so that the cannulated plug or screw with the engaged eyelet implant is flush with the bone.

U.S. Application Publication No. 2008/0004659, the disclosure of which is incorporated by reference herein, discloses a technique and device for knotless fixation of tissue using a swivel anchor. According to this technique, a swivel anchor having a rotatable forked anchor tip is used to capture suture for surgical tissue repair without requiring suture knots. Tension on the repair constructs is adjustable through the selection of a specific chain link or links of the suture chain captured by a forked anchor tip of the swivel anchor. The swivel anchor is secured in a hole in bone by advancing a fixation device, such as a cannulated interference screw, over the body of the anchor.

Although the above-described techniques provide improved methods of graft fixation to bone through knotless fixation, it is not evident how to accomplish in situ surgical refinements such as getting a hard stop on a suture without relying on friction. Accordingly, there is a need in the art for improved technology for knotless tissue fixation.

SUMMARY OF THE INVENTION

The present invention fulfills the needs noted above by providing a knotless tissue fixation technique by capturing and anchoring a link of a chain (for example, a suture chain) attached to tissue. The technique of the present invention utilizes a push-in type anchor (for example, a self-punching anchor) and a chain that includes a plurality of loops (for example, a plurality of suture loops). A first portion of the chain is secured to the tissue to be fixated. The chain is next secured to the push-in type anchor (for example, by passing the chain through an eyelet of the anchor). The anchor is then advanced along the chain to bring a tip of the anchor above a chosen loop or link of the chain. The tip of the anchor is pushed through the chosen loop so that the tip locks the chosen loop in place (for example, by capturing both sides of the link above a shoulder of the anchor). With the captured link, the anchor is advanced into a pilot hole or socket formed in the bone to fixate the tissue. A fixation device such as a cannulated interference screw may be advanced over the body of the anchor to complete fixation of the tissue to bone.

The technique of the present invention may be employed with various methods of knotless fixation of tissue to bone. An exemplary link-lock double-row technique of the present invention includes the steps of: (i) placing a medial anchor pre-loaded with a suture chain that includes a plurality of loops; (ii) passing the suture chain through soft tissue (for example, rotator cuff tear); (iii) capturing a loop or link of the suture chain with a tip of an anchor (such as a self-punching PushLock SP™ anchor) so that the anchor locks in the chosen loop; and (iv) laterally fixating the anchor with the captured loop into a lateral bone socket. The knotless technique provides a hard stop that will not slip (in addition to the standard frictional interference of the suture chain between the anchor and the bone) as opposed to the standard interference-fit techniques which rely primarily on friction for fixation.

These and other features and advantages of the present invention will become apparent from the following description of the invention that is provided in connection with the accompanying drawings and illustrated embodiments of the invention.

DETAILED DESCRIPTION OF THE PREFERRED EMBODIMENTS

Figure 1:
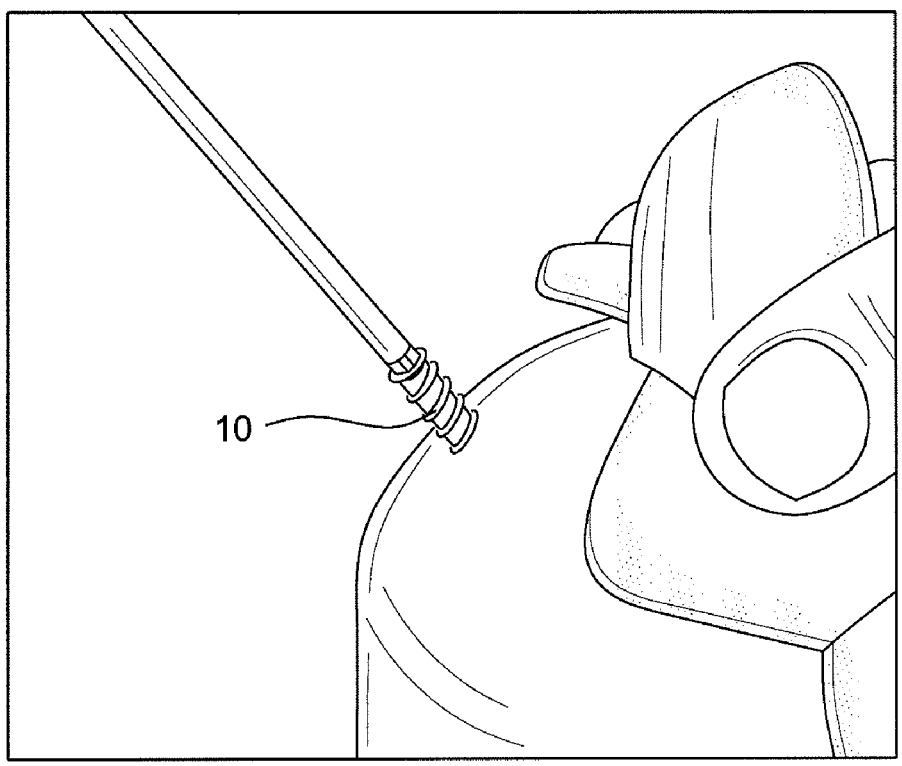
FIGS. 1-10 illustrate the technique of the present invention.

The present invention provides methods and apparatus for conducting anatomical tissue repair, such as ligament repair and reconstruction, by capturing and anchoring a link of suture chain attached to tissue.

The technique of the present invention utilizes a push-in type anchor (for example, a self-punching anchor) and a suture chain that includes a plurality of loops.

In one embodiment, a first portion of the suture chain is secured to the tissue to be fixated. The suture chain is next secured to the push-in type anchor (for example, by passing the suture chain through an eyelet of the anchor). The anchor is then advanced along the suture chain to bring a tip of the anchor above a chosen loop or link of the suture chain. The tip of the anchor is pushed through the chosen loop so that the tip locks the chosen loop in place (for example, by capturing both sides of the link above a shoulder of the anchor). With the captured link, the anchor is advanced into a pilot hole or socket formed in the bone to fixate the tissue. A fixation device such as a cannulated interference screw may be advanced over the body of the anchor to complete fixation of the tissue to bone.

According to another embodiment, the link-lock method of the present invention provides attaching soft tissue (for example, tendon or rotator cuff) to bone by a double-row technique (explained below with reference to FIGS. 1-10). The double-row technique of the present invention includes the steps of: (i) providing a first medial row constructed with a first plurality of fixation devices, at least one of the first plurality of fixation devices being an anchor pre-loaded with a suture chain; (ii) passing the suture chain through soft tissue; (iii) securing the suture chain to a knotless fixation device (by threading the suture chain through a body of the knotless fixation device, for example); (iv) capturing at least one link of the suture chain with a tip of the knotless fixation device; and (v) fixating (into a lateral bone socket) the captured link and the knotless fixation device, to provide a second lateral row constructed with a second plurality of fixation devices, at least one of the second plurality of fixation devices being the knotless fixation device with the captured link. The suture chain extends over the soft tissue and is secured in place by the knotless fixation device.

In an exemplary embodiment, the double-row technique of the present invention includes the steps of: placing a medial anchor pre-loaded with a FiberChain®; passing the FiberChain® through the soft tissue (for example, rotator cuff tear); capturing a loop or a link of the FiberChain® with a tip of a suture anchor (such a self-punching PushLock SP™ anchor); and laterally fixating the suture anchor with the captured loop into a lateral bone socket. The knotless technique provides a hard stop that will not slip (in addition to the standard frictional interference of the suture chain between the anchor and the bone) as opposed to the standard interference-fit techniques which rely primarily on friction for fixation.

In an exemplary and illustrative embodiment only, the technique of the present invention utilizes a self-punching PushLock SP™ anchor along with a FiberChain®. This technique has elements of the two techniques described above (in U.S. Patent Application Publication No. 2008/0208253 and U.S. Patent Application Publication No. 2008/0004659), which makes it superior to both the techniques. One of the advantages of the technique of the present invention is that it is possible to get a hard stop without relying on friction. Further, it is possible to thread a FiberChain® through an anchor with the FiberChain® coming out through the same portal, so that a given link need not be captured inside the shoulder as in the above-described swivel anchor technique.

In one embodiment of the invention, pilot holes or sockets are created in the bone at the locations that the graft is to be secured. An anchor, preferably a fully threaded Bio-Corkscrew® preloaded with a FiberChain®, sold by Arthrex, Inc., Naples, Fla., is placed in a medial portal. The FiberChain® is passed using a suture passer, preferably a Scorpion™ Suture Passer, sold by Arthrex, Inc., Naples, Fla. The FiberChain® is pulled out through an anterolateral portal and threaded through an eyelet of a self-punching PushLock SP™ anchor. The PushLock SP™ is advanced along the FiberChain® and the PushLock SP™ anchor is turned, preferably in a clockwise direction, to bring a tip of the PushLock SP™ anchor above a chosen link. Typically, the chosen link is the second or the third link from the edge of a rotator cuff. Alternatively, the PushLock SP™ anchor may be advanced along the entire FiberChain®, without turning the PushLock SP™ anchor, but this results in greater friction on the FiberChain®.

The tip is pushed through the chosen link to capture both sides of the link above the shoulder of the PushLock SP™ anchor tip so that the tip locks the chosen link in place. The FiberChain® link is securely captured above the shoulders of the tip of the self-punching PushLock SP™ anchor. The tip of the PushLock SP™ anchor is inserted into the bone socket, to get good compression over the top of the rotator cuff.

A fixation device or anchor is fully advanced into the pilot hole or socket behind the tip of the PushLock SP™, so that the anchor is flush with the bone. Once the anchor is fully inserted and the PushLock SP™ anchor and FiberChain® are secured in the pilot hole or socket, any loose ends of the FiberChain® protruding from the anchor site are then clipped short.

Referring now to the drawings, where like elements are designated by like reference numerals, FIGS. 1-10 illustrate the technique under dry lab conditions. Details of the various instruments, accessories and implants used in the link-lock technique are listed below in Table 1.

TABLE 1

| List of Instruments, Accessories and Implants | |
|---|---|
| PushLock SP ™ | |
| Description: | The PushLock SP was developed to help speed completion of a suture bridge while increasing the precision of the final construct. It combines a small titanium tip with either a PLLA or PEEK anchor body. The titanium tip minimizes the need to prepare a bone socket for the lateral row, where soft tissue can sometimes obscure the view. The self-punching feature helps maintain proper axial alignment of the anchor during its final insertion into the bone socket. |
| Bio-Corkscrew ® | |
| Description: | A bioabsorbable PLLA suture anchor that has 14 inch pounds of insertion torque strength. The strong internal drive mechanism provides double the resistance to stripping than any other bioabsorbable suture anchor available. |
| Bio-SwiveLock ™ C | |
| Description: | A 4.75 mm or 5.5 mm twist-in knotless anchor. This anchor functions very similar to the PushLock but with a twist-in design. This anchor is available with a bioabsorbable PLLA anchor body and PEEK eyelet. It can be used as the lateral row of the suture bridge. It can also be combined with FiberTape ®. |
| Scorpion ™ Suture Passer | |
| Description: | Ergonomically designed for one-hand use, the multi-function suture passer can grasp rotator cuff tissue and retrieve a suture. |
| KingFisher ® Suture Retriever/Tissue Grasper | |
| Description: | It is used for arthroscopic tissue grasping/reduction and has a self-releasing jaw lock mechanism. To lock the jaws, and securely hold the tissue, pressure is applied |

TABLE 1-continued

List of Instruments, Accessories and Implants

| | |
|---|---|
| | on the posterior aspect of the forward finger. To release the lock, and open the jaws, finger pressure is transferred to the anterior portion of the forward ring.<br>FiberChain ® |
| Description: | A single stranded #2 FiberWire ® suture strand that transitions to chain links of interwoven FiberWire ®. The FiberWire ® suture is a multi-stranded long chain ultra-high molecular weight polyethylene (UHMWPE) core with a braided jacket of polyester and UHMWPE.<br>FiberTape ® |
| Description: | An ultra-high strength 2 mm tape using an ultrahigh molecular weight polyethylene structure. |

Figure 2:
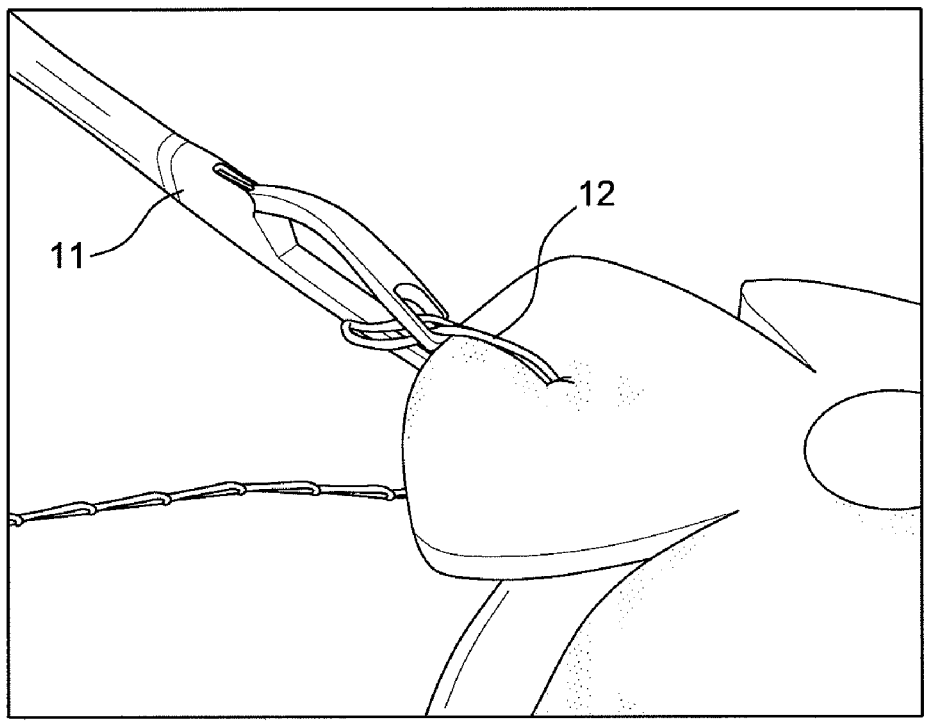
Figure 3:
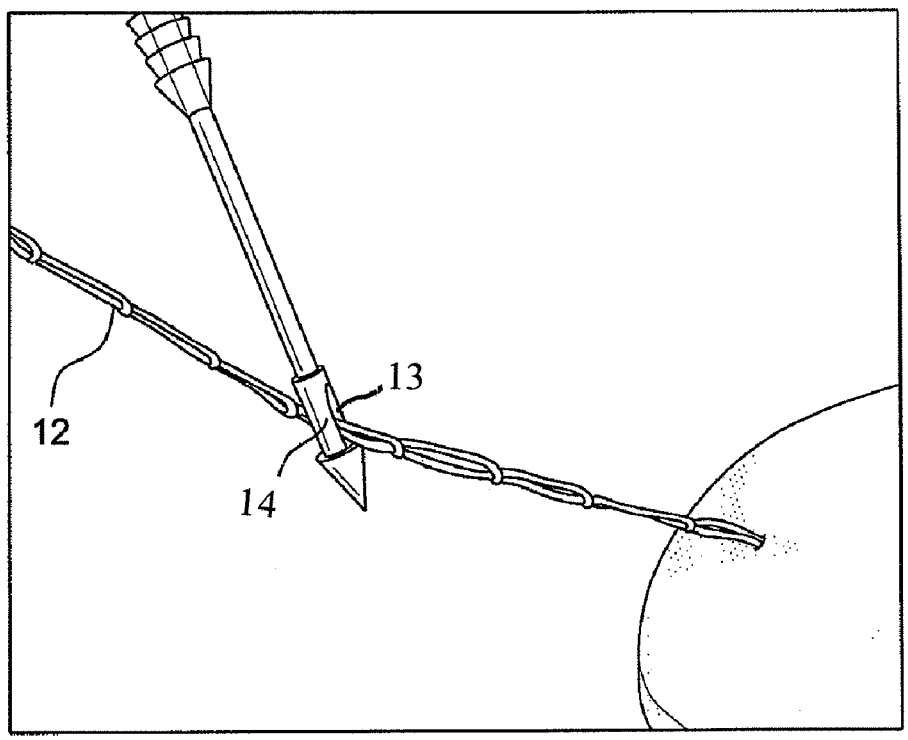

Referring to FIG. 1, an anchor 10, for example, a fully threaded Bio-Corkscrew® preloaded with FiberChain®, is placed in a medial portal. The FiberChain® 12 is passed using a Scorpion™ suture passer 11 and the FiberChain® 12 is pulled out through an anteriolateral portal, as shown in FIG. 2. The FiberChain® 12 is threaded through an eyelet 13 of the tip or implant 15 of a self-punching PushLock SP™ anchor 14, as shown in FIG. 3.

Figure 4:
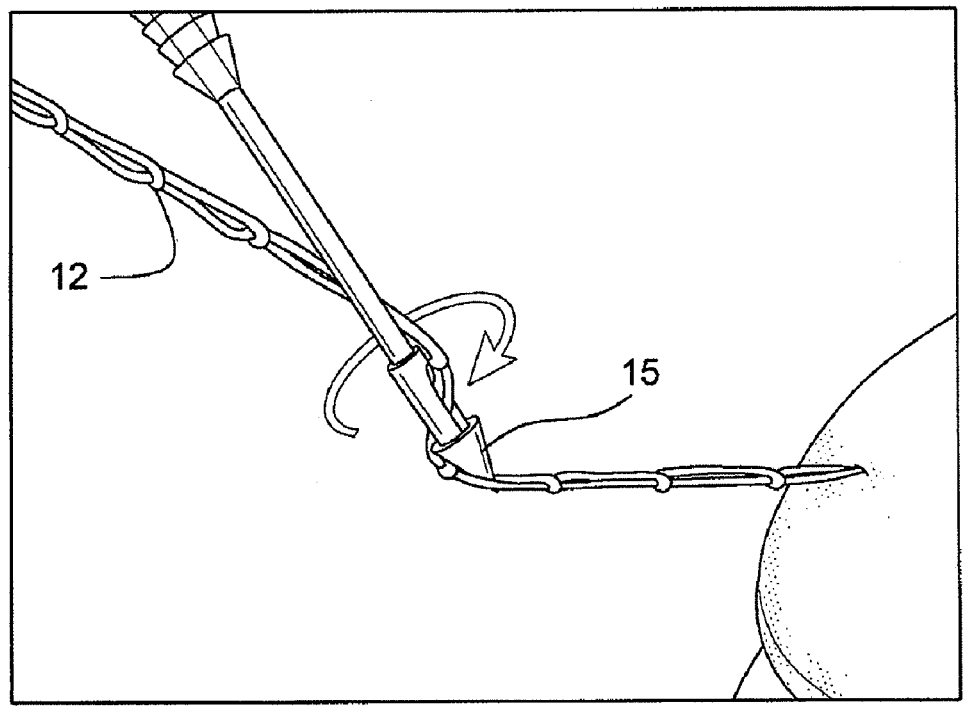
Figure 5:
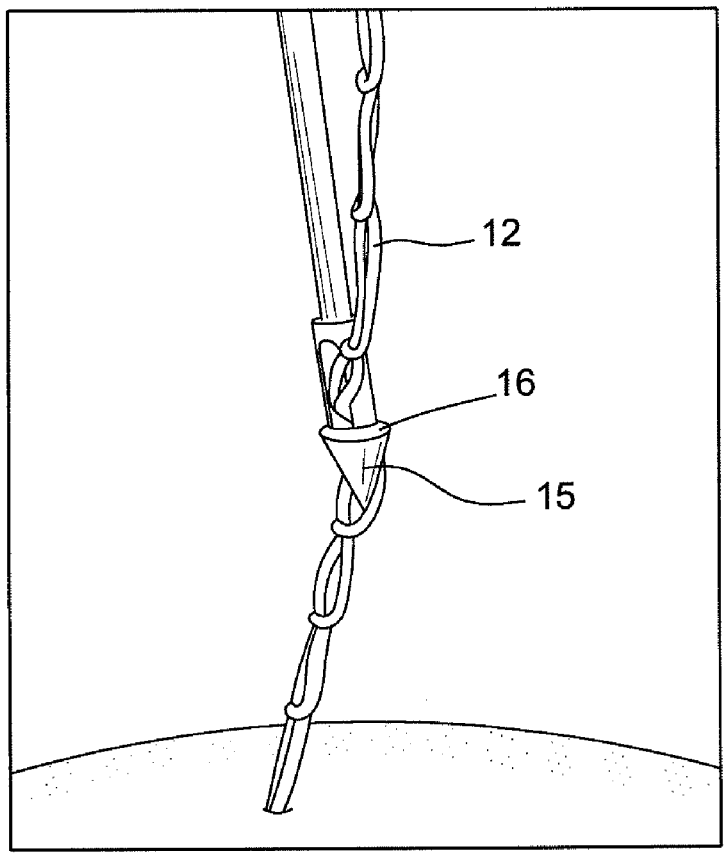
Figure 6:
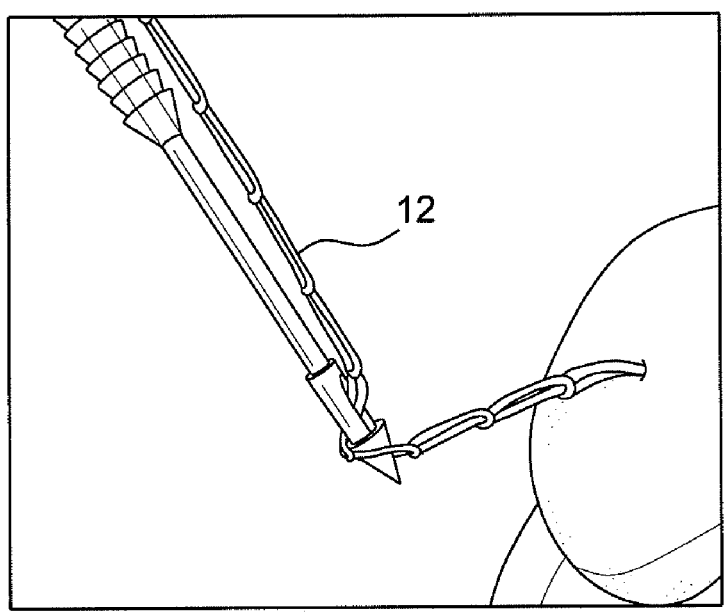
Figure 7:
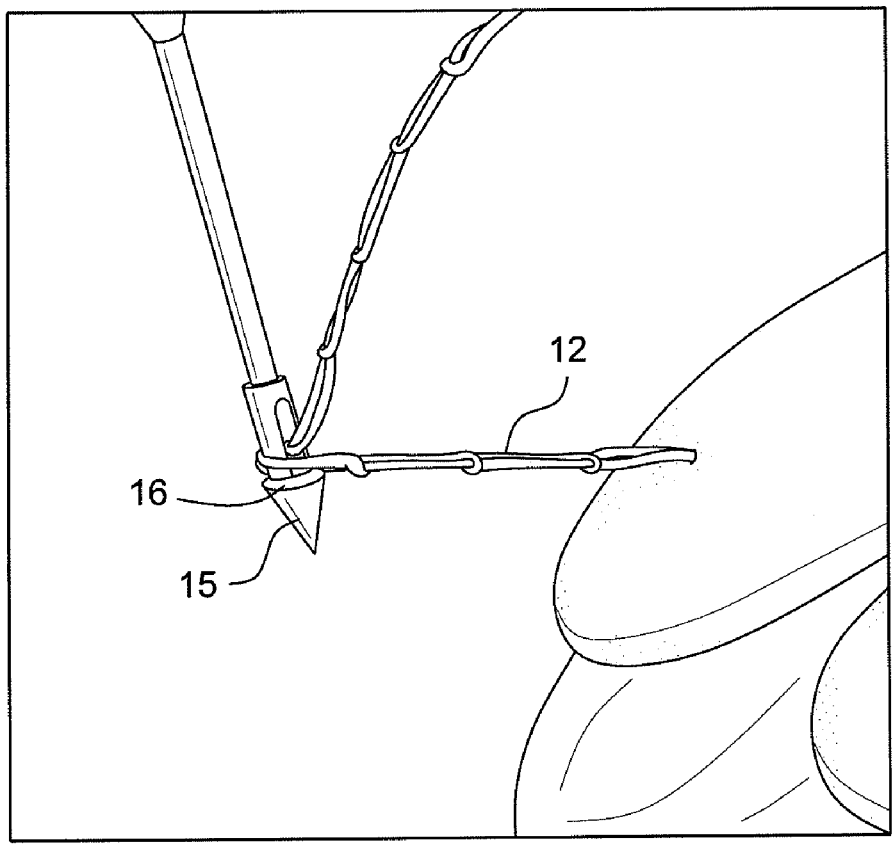

Next, referring to FIG. 4, the PushLock SP™ anchor is advanced along the FiberChain® 12 and the PushLock SP™ anchor is turned in a clockwise direction to bring the tip 15 above a chosen link of the FiberChain® 12, typically the second or the third link from a rotator cuff edge. Alternatively, the PushLock SP™ anchor may be advanced along the entire FiberChain®, without turning the PushLock SP™ anchor, but this may result in greater friction on the FiberChain®.

Figure 8:
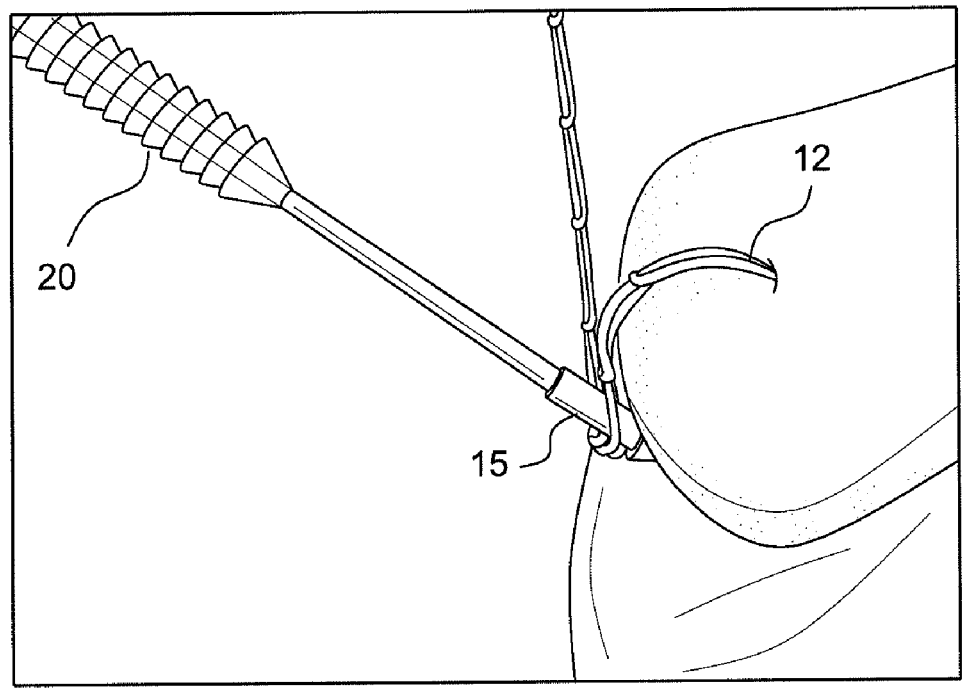
Figure 9:
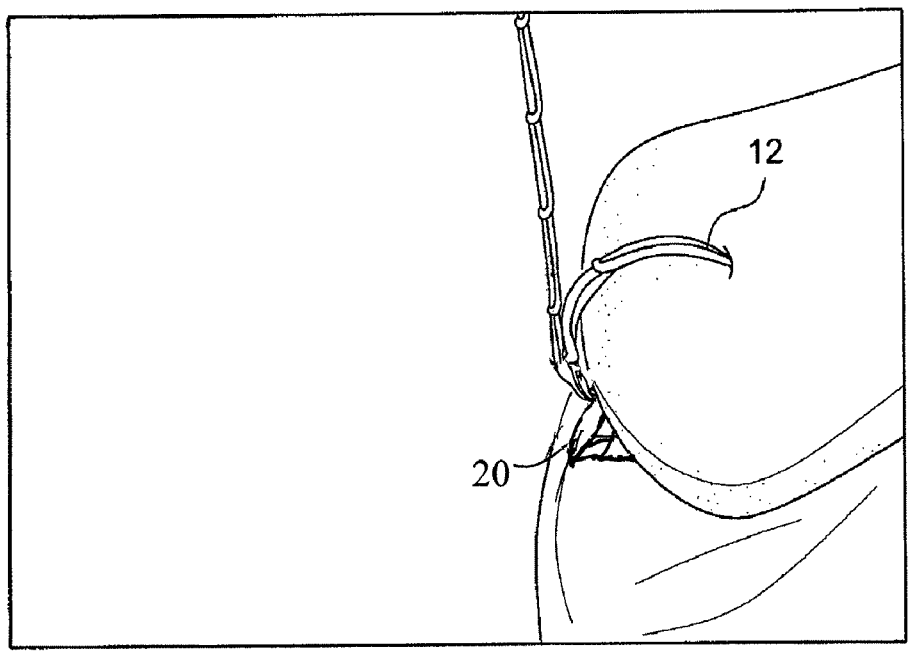
Figure 10:
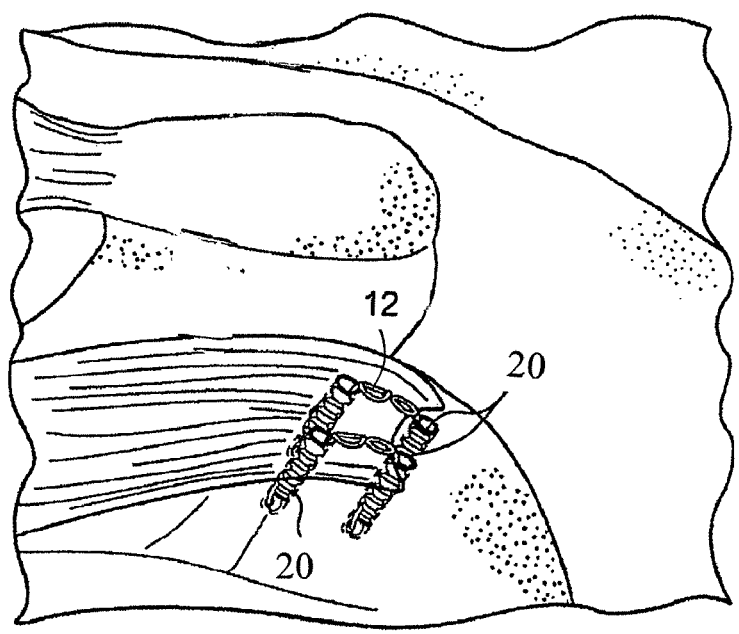

Referring to FIGS. 5-10, the tip 15 of the PushLock SP™ anchor 14 is pushed through the chosen link to capture both sides of the link above a shoulder 16 of the anchor tip 15, so PushLock SP™ anchor 14 securely captures the chosen link in place. Next, the PushLock SP™ anchor tip 15 is pushed into a bone socket, as shown in FIG. 8, to get good compression over the top of the rotator cuff. A fixation device or anchor 20 is then impacted into the bone socket, using a standard push lock technique, so that the anchor 20 advances toward a distal end of the PushLock SP™ anchor 14 and securely engages and locks the FiberChain® 12 in the bone socket (FIG. 9). After the anchor 20 is fully inserted in the bone socket, the ends of the FiberChain® 12 can be removed by clipping them short, leaving the graft securely fastened to bone. FIG. 10 illustrates a first medial row constructed with a first plurality of fixation devices 20 and a second lateral row constructed with a second plurality of fixation devices 20 with the suture chain 12 extending over the soft tissue.

A significant advantage of the present invention is that the sutures attached to the graft or the graft itself can be securely attached to the bone without the need to tie knots. Additionally, a hard stop is achieved, instead of a friction stop, and suture can be threaded through a single cannula.

Although the terms "chain," "suture chain" and FiberChain® have been used interchangeably in this application, it must be understood that the term "chain" is not limited to only "suture chain" or FiberChain®; rather, the term "chain" encompasses a plurality of loops of any material and of any dimension (i.e., loops of similar or different diameters), as long as the loops are interconnected to each other. An exemplary suture chain that may be used in the present application is described in U.S. Patent Appl. Publ. No. 2007/0135843, the disclosure of which is incorporated by reference in its entirety herewith.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A method of knotless tissue fixation comprising:
   providing a suture chain that includes at least two loops formed of suture;
   securing a first portion of the suture chain to a tissue to be fixated;
   attaching the suture chain to a bone anchor by threading the suture chain through an eyelet of the anchor;
   advancing the anchor along the suture chain by rotating the anchor to bring a tip of the anchor over a chosen loop of the suture chain;
   capturing the chosen loop of the suture chain with the anchor by pushing the tip of the anchor through the chosen loop so that the tip locks the loop over a shoulder of the fixation device;
   inserting the anchor and the captured link into bone; and
   subsequently, securing the anchor and the captured loop into the bone.

2. The method of claim 1, wherein the bone anchor is a push-in type anchor.

3. The method of claim 1, wherein the anchor is a push-in anchor with a shouldered tip.

4. The method of claim 1, wherein the anchor is inserted into a pre-formed socket in the bone.

5. A method of knotless tissue fixation comprising:
   providing a suture chain that includes at least two loops formed of and connected by suture;
   providing a bone socket;
   securing a first portion of the suture chain to a tissue to be fixated;
   threading a second portion of the suture chain through an eyelet of an anchor;
   subsequently, advancing the anchor along the suture chain by turning the anchor to advance a tip of the anchor over a chosen loop of the suture chain and pushing the tip of the anchor through the chosen loop to capture the loop of the suture chain with the tip of the anchor; and
   securing the captured loop into the bone socket.

6. The method of claim 5, wherein the step of securing the captured loop into the bone socket further comprises anchoring the suture chain into the bone socket using the anchor and a fixation device, thereby providing tissue fixation.

7. The method of claim 6, wherein the fixation device is a cannulated interference screw.

8. The method of claim 5, wherein the anchor is a push-in type anchor.

9. A method of attaching soft tissue to bone without tying a knot comprising:
   providing a first medial row constructed with a first plurality of anchors, wherein at least one of the first anchor is pre-loaded with a suture chain that includes at least two loops formed of and connected by suture; and providing a second lateral row constructed with a second plurality of anchors, wherein at least one of the second anchors is a knotless anchor, the knotless anchor being configured to capture at least two different regions of the suture chain with two different parts of the knotless anchor, and to secure the suture chain in a socket in bone;

positioning a tip of the knotless anchor over a suture loop and pushing the tip through the suture loop so that the tip locks the loop over a shoulder of the anchor inserting the anchor with the captured loop into the bone socket; and securing the captured loop and the anchor in the bone socket using a fixation device.

10. The method of claim 9, wherein the anchor is a push-in type anchor.

11. A method of attaching soft tissue to bone comprising:

placing a medial anchor pre-loaded with a suture chain that includes at least two loops;

passing the suture chain through the soft tissue;

threading the suture chain through an eyelet of a knotless anchor;

advancing the knotless anchor over the suture chain to position the tip of the anchor over a chosen loop of the suture chain;

pushing the tip through the chosen loop so that the tip locks the loop over a shoulder of the tip; and securing the suture chain with the anchor in a hole in bone, the hole being provided lateral to the medial anchor.

12. The method of claim 11, wherein the suture chain provides both a hard stop that does not slip and frictional interference between the knotless fixation anchor and the bone socket.

* * * * *